United States Patent [19]
Sandine et al.

[11] Patent Number: 5,654,020
[45] Date of Patent: Aug. 5, 1997

[54] METHOD USING LACTOBACILLUS AS-1 FOR INHIBITING FOOD SPOILAGE

[75] Inventors: William E. Sandine; Nageb Al-Zoreky, both of Corvallis, Oreg.

[73] Assignee: Oregon State University, Corvallis, Oreg.

[21] Appl. No.: 480,550

[22] Filed: Jun. 7, 1995

Related U.S. Application Data

[63] Continuation of Ser. No. 951,809, Sep. 28, 1992, abandoned

[51] Int. Cl.⁶ .................................................. A23C 9/12
[52] U.S. Cl. .......................... 426/42; 426/34; 426/43; 426/58
[58] Field of Search .............................. 426/34, 42, 43, 426/55, 56, 580, 581, 582, 583, 586, 587; 435/252.1, 252.9

[56] References Cited

U.S. PATENT DOCUMENTS

| | | |
|---|---|---|
| 4,599,313 | 3/1984 | Gonzalez . |
| 4,874,704 | 10/1989 | Boudreaux et al. .................. 426/61 |
| 4,912,047 | 3/1990 | Matrozza et al. ................. 435/252.9 |
| 5,186,962 | 2/1993 | Hutkins et al. .................... 426/61 |

OTHER PUBLICATIONS

Darmadji et al., 91 (04): S0061 FSTA, Abstracting Journal of Food Science, (1990) 55 (6) 1523–1527.
Lee et al., 69(08): B0324 FSTA, Abstracting Bacteriological Proceedings, (1969) 1969: 13.
Abdel–Bar et al., 84 (09): B0121 FSTA, Abstracting Journal of Food Protection, (1984), 47 (1) 61–64.
Potter, N.N., Food Science, Third Edition, 1978, pp. 378–379, AVI Publishing Company, Inc. (Westport).
Fontaine, E.A., et al. Journal of Applied Bacteriology, 69, 326–331 (1990).
White, et al., J. Food Protection 42, 51–54 (1979).
Griffiths, et al., J. Soc. Dairy Tech. 44, 24–29 (1991).
Marshall, et al., Can. J. Microbiol. 37, 594–599 (1991).
Roberts and Torrey (J. Dairy Sci. 71:52–60 (1988).

*Primary Examiner*—Leslie Wong
*Attorney, Agent, or Firm*—Ian C. McLeod

[57] ABSTRACT

A novel strain, Lactobacillus sp. AS-1 (ATCC No. 55326) for use in inhibiting bacteria in foods, particularly at refrigeration temperatures. Lactobacillus sp. AS-1 (ATCC No. 55326) is particularly effective in inhibiting bacteria present in raw milk and pasteurized milk.

7 Claims, 3 Drawing Sheets

METHOD USING LACTOBACILLUS AS-1 FOR INHIBITING FOOD SPOILAGE

This is a continuation of application Ser. No. 07/951,809, filed on Sep. 28, 1992, now abandoned.

BACKGROUND OF THE INVENTION

(1) Field of the Invention

The present invention relates to a method and bacterial compositions which use cells of Lactobacillus sp. AS-1 (ATCC No. 55326) to inhibit spoilage in foods. In particular, the present invention relates to a lactic acid producing bacterium which can be used to prevent spoilage in foods at refrigeration temperatures and which does not produce significant amounts of lactic acid in the food.

(2) Prior Art

Lactic acid bacteria have been used to inhibit pathogens and spoilage bacteria in milk and other foods as evidenced by U.S. Pat. Nos. 4,599,313 to Gonzalez and 4,912,047 to Matrozza and by White et al., J. Food Protection 42, 51–54 (1979) and Griffiths et al, J. Soc. Dairy Tech. 44, 24–29 (1991). A paper was presented in a meeting of the Institute of Food Technologists in June, 1991 describing the use of lactic acid bacteria in milk to inhibit pathogens and spoilage. The specific strain used was not identified or described. The bacterial compositions described are effective; however, there is a need for a more effective bacterial composition, particularly one for use in raw milk. One particular problem is that most lactic acid bacteria of the prior art produce sufficient lactic acid even at low temperatures so as to render raw milk unsuitable for pasteurization. Heating raw milk in pasteurizer units when the milk pH is 5.0 or below causes deposit of denatured milk proteins on heating surfaces.

In some countries several days may elapse before raw milk is pasteurized. During that time pathogens and spoilage bacteria can grow and render the milk unfit for its intended use. The legal bacterial count of raw milk is $1 \times 10^5 - 3 \times 10^5$ (100,000 for individual producers—300,000 for co-mingled milk) colony-forming units (CFU)/ml. Psychrotrophic bacteria grow at low temperatures (4°–5° C. or 40°–41° F.) and degrade proteins and fat of raw milk and enzymes from these bacteria survive even ultra high temperature (UHT) pasteurization.

Temperature abuse occurs and spoilage and pathogenic bacteria grow reducing quality and safety of the raw milk. Raw milk is stored at 40° F. before pasteurization for transportation to dairy plants. There may be a short supply of raw milk to large dairy plants and thus there is a need for a reliable and effective method for preserving the raw milk.

The problems with raw milk are present with other refrigerated foods where temperature abuse can occur. Fluid or semi-fluid dairy products, such as yogurt, sour cream, cream and cottage cheese particularly have problems.

OBJECTS

It is therefore an object of the present invention to provide a Lactobacillus sp. which is uniquely suited to inhibiting spoilage in foods. It is particularly an object of the present invention to provide a Lactobacillus sp. which inhibits spoilage in raw milk and other refrigerated fluid dairy products. These and other objects will become increasingly apparent by reference to the following description and the drawings.

IN THE DRAWINGS

GENERAL DESCRIPTION

The present invention relates to a method for inhibiting bacteria in a refrigerated food by introducing a bacterium into the food, the improvement which comprises providing an effective amount of Lactobacillus sp. AS-1 (ATCC No. 55326) in the refrigerated food to thereby inhibit the psychrotrophic bacteria.

Further the present invention relates to a method of inhibiting bacteria in refrigerated raw milk by introducing a Lactobacillus into the raw milk, the improvement which comprises providing cells of Lactobacillus sp. AS-1 (ATCC No. 55326) in the raw milk, wherein the Lactobacillus sp. inhibits bacteria in the raw milk.

Finally the present invention relates to a bacterial composition which comprises cells of Lactobacillus sp. AS-1 (ATCC No. 55326) free of other cells.

The term "spoilage" means the growth of pathogens in the food or the growth of psychrotrophic bacteria in the food. In either case the food is spoiled.

The foods which can be preserved are raw milk, pasteurized milk or cream of various milk or vegetable fat contents, Cottage cheese, cream cheese, Mexican style white cheese, cultured buttermilk, cultured sour cream, butter and the like. In particular, refrigerated dairy products, such as raw milk, Cottage cheese, sour cream, cream yogurt and the like can be preserved by the methods and compositions of the present invention.

Lactobacillus sp. AS-1 (ATCC No. 55326) was deposited under the Budapest Treaty with the American Type Culture Collection in Rockville, Md. Lactobacillus sp. AS-1 ATCC 55326 was redeposited as ATCC 69890 on Aug. 17, 1995 as AS-1A after elimination of some cells which contaminated the original deposit ATCC 55326. The characteristics of this strain are shown in Table 1.

TABLE 1

| | |
|---|---|
| 1. Morphology | Coccobacilli (oval, in pairs and short chains |
| 2. Catalase | Negative |
| 3. Gram Reaction | Positive |
| 4. Type of Fermentation | Heterofermentative |
| 5. Gas from glucose (MRS broth) | Positive |
| 6. Type of lactic acid produced | DL-lactic |
| 7. Growth at 10° C. (in MRS broth) | Positive |
| 8. Growth at 30° C.[(1)] " | Positive |
| 9. Growth at 37° C. " | Positive |

TABLE 1-continued

| | |
|---|---|
| 10. Growth at 45° C. " | Positive |
| 11. Growth at 50° C. " | Negative |
| 12. Final pH in MRS broth with incubation at 30° C. for 24 hours | 4.4–4.6 |
| 13. Utilization of carbohydrates: | |
| glucose | Positive |
| galactose | Positive |
| fructose | Positive |
| lactose | Positive |
| xylose | Negative |
| rhamnose | Negative |

(1)Recommended temperature for activation and inhibition studies.

The culture is used at a level of about $10^6$ to $10^8$ cells per ml or gram of the food. The food is preferably refrigerated at between about 4° and 6° C.

Lactobacillus can be preserved for shipment by freezing, using various well known agents such as glycerol, sucrose and milk. The culture can also be lyophilized for shipment. Preferably the lyophilizing agent is milk.

SPECIFIC DESCRIPTION

Example 1

Figure 1A:
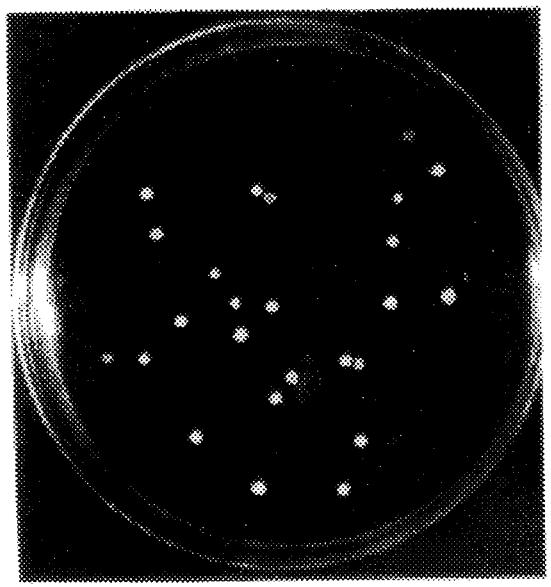
FIGS. 1A and 1B are photographs showing the quantity of gram negative bacteria present when raw milk inoculated with $10^2$ Pseudomonas aeruginosa per ml and incubated at 2°–5° C. for 7 days in the presence FIG. 1A or absence FIG. 1B of inhibitory Lactobacillus sp. AS-1 (ATCC No. 55326) after spread plating on CVT agar and incubating at 32° C. for 48 hours.
Figure 1B:
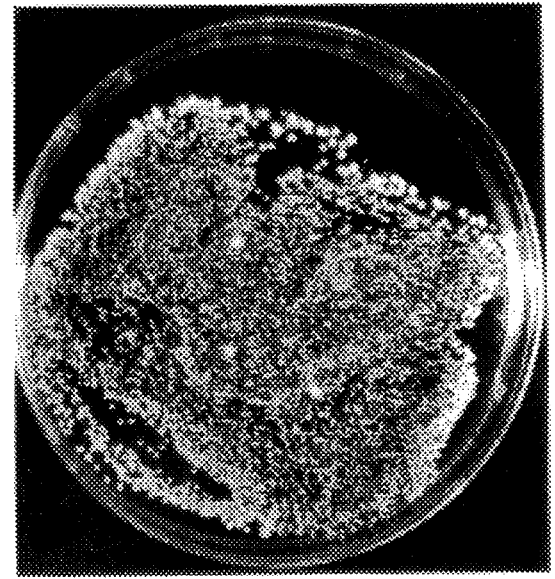
Figure 2A:
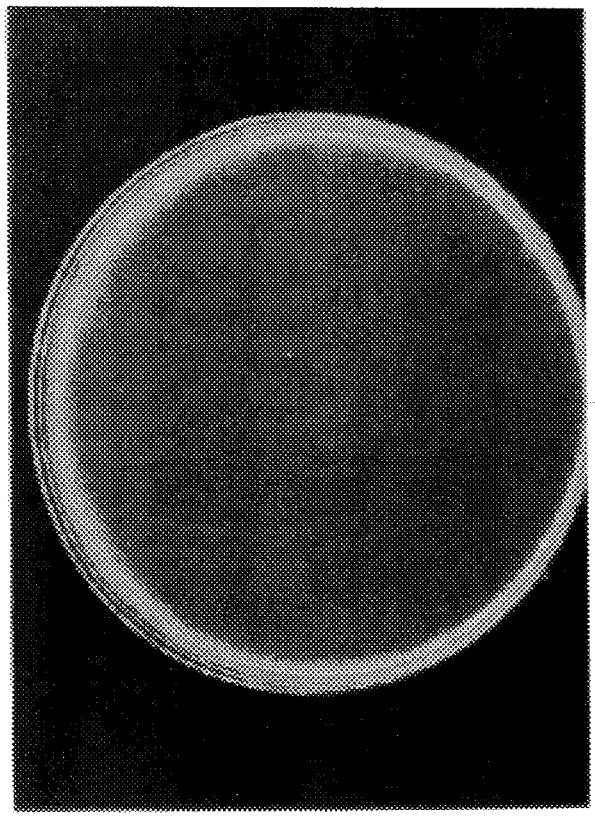
FIGS. 2A and 2B are photographs showing spiral plate enumeration of bacteria present in 50 µl of raw milk held 6 days at 40° F. in the presence of $10^7$ CFU/ml of Lactobacillus sp. As-1 (ATCC No. 55326) FIG. 2A or absence of ATCC No. 55326 FIG. 2B after incubation of plates of Pseudomonas isolation agar 48 hours at 30° C.
Figure 2B:
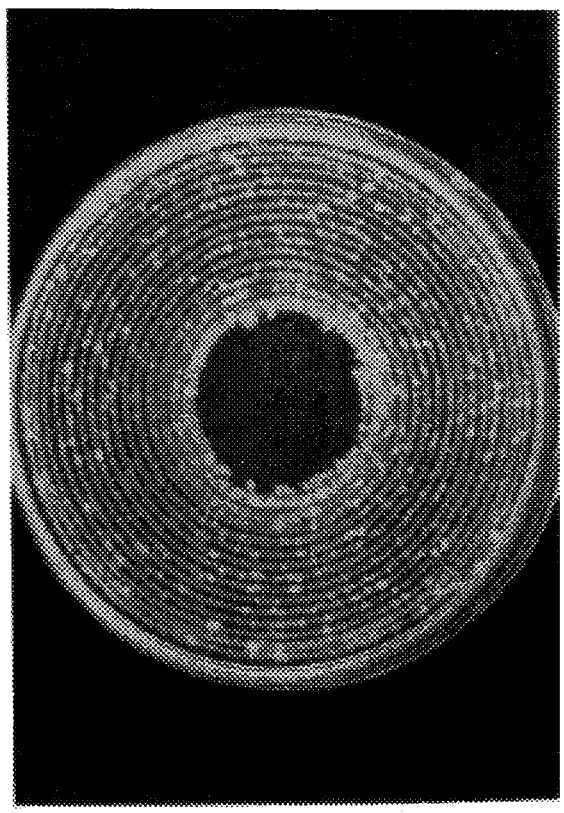
Figure 3A:
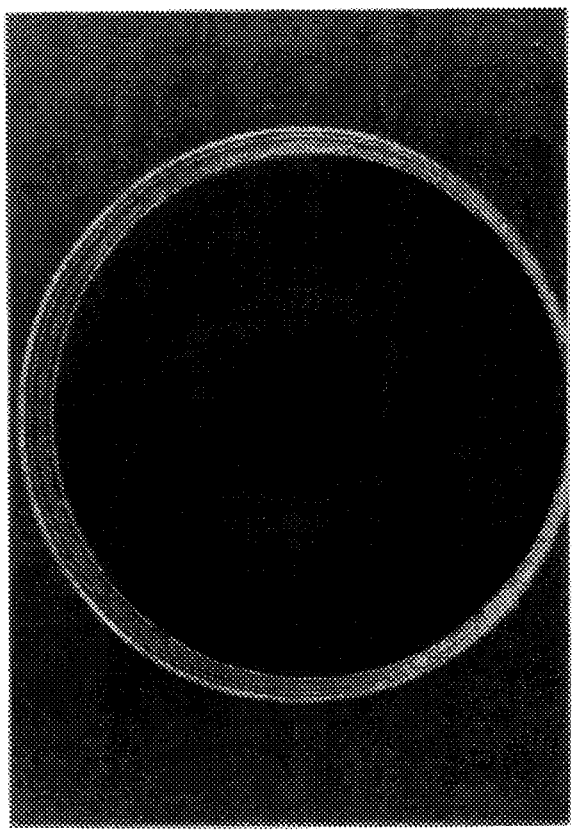
FIGS. 3A and 3B are photographs showing spiral plate enumeration of bacteria present in 50 µl of raw milk held 6 days at 40° F. in the presence of $10^7$ CFU/ml of Lactobacillus sp. AS-1 (ATCC No. 55326) FIG. 3A or absence of ATCC No. 55326) FIG. 3B after incubation of plates of MacConkey agar at 37° C. for 48 hours.
Figure 3B:
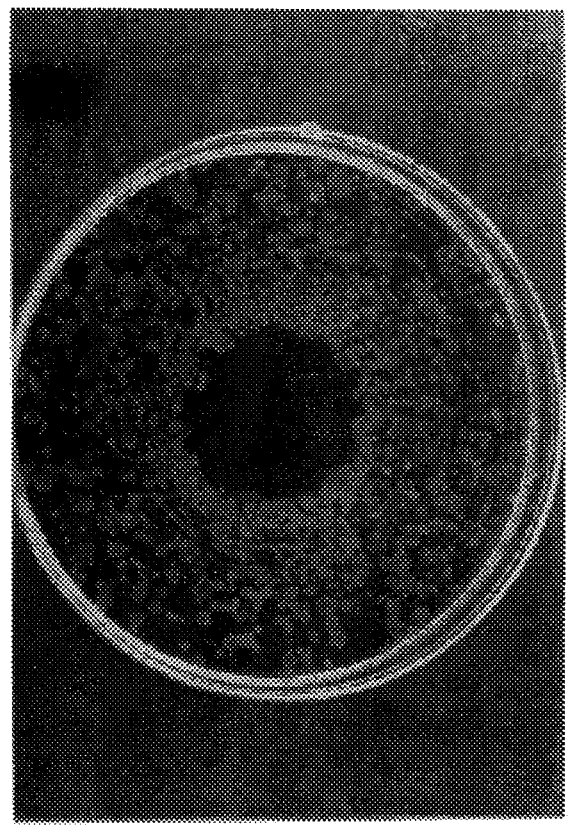

Lactic acid producing bacteria were screened for their ability to inhibit other spoilage bacteria when the former are added to fresh raw milk which is held at 2°–5° C. FIGS. 1A and 1B illustrate the ability of a Lactobacillus species (ATCC No. 55326) to inhibit *Pseudomonas aeruginosa* (ATCC No. 419). The photo shows the microbial condition of the milk after holding for 7 days in the presence of the Lactobacillus FIG. 1A or the absence FIG. 1B. At 2°–5° C., raw milk inoculated with *P. aeruginosa* supports luxuriant growth of the organism while a duplicate sample of the same milk inoculated with 3% of an overnight culture ($10^7$ cells per ml or gram) of the Lactobacillus species failed to support such growth. The added *P. aeruginosa* (~100/ml) grew to $10^8$/ml in plain raw milk at 2°–5° C. while the Lactobacillus—supplemental milk maintained the same count for total Gram negative bacteria as the zero time control raw milk (~100/ml). Samples of the raw milk were plated by spreading on CVT agar, which is Standard Plate Count agar containing 1 ppm of 2, 3, 5-triphenyltetrazolium chloride and 50 ppm of crystal violet. This medium allows Gram negative bacteria to grow but inhibits gram positive types such as the added Lactobacillus sp. ATCC No. 55326.

Example 2

In this example, the CFU/ml in raw milk for Lactobacillus AS-1 was $\geq 1.2 \times 10^7$. The raw milk was stored at 40°–41° F. for six days and then tested. Pseudomonas isolation agar and MacConkey agar (Difco, Detroit, Mich.) were used to enumerate Pseudomonas spp. and other Gram-negative bacteria including Salmonella spp., respectively.

The CFU/ml in the milk was $<4 \times 10^2$ at zero time for Pseudomonas or the other Gram-negative bacteria. Without any treatment, after 3 days of storage of the raw milk at 40° F., the CFU/ml was $10^4$, and after 6 days storage of the raw milk at 40° F., the CFU/ml was $10^6$.

With the addition of active culture of Lactobacillus ATCC No. 55326 ($\geq 10^7$ml) to raw milk at zero time, the CFU/ml of group was $<10^2$ after storage for six days at 40° F. as shown in FIGS. 2A, 2B, 3A and 3B.

Example 3

*P. putida* was added to raw milk at four different levels and raw milk was stored at 40° F. for six days. Duplicate samples of the raw milk containing the four levels of *P. putida* were challenged with $\geq 10^7$ CFU/ml of Lactobacillus sp. ATCC No. 55326.

Four levels of *P. putida* used were:

(1) $1 \times 10^5$/ml
(2) $2.5 \times 10^3$/ml
(3) $<10^3$/ml
(4) $<10^2$/ml

Lactobacillus sp. ATCC No. 55326 was used at a level of $10^7$ CFU/ml. Table 2 shows the results of the treatment with *P. putida* using the selective medium of Example 2 after cold storage (40°–41° F.) of raw milk for different day periods.

TABLE 2

| | 3-day | 5-day | 6-day |
|---|---|---|---|
| Level (1) alone | >$10^7$ | >$10^7$ | >$10^7$ |
| Level (1) + ATCC 55326 | $10^4$ | $10^4$ | $10^4$ |
| Level (2) alone | >$10^6$ | >$10^7$ | >$10^7$ |
| Level (2) + ATCC 55326 | $10^3$ | $10^3$ | $10^3$ |
| Level (3) alone | >$10^4$ | >$10^7$ | >$10^7$ |
| Level (3) + ATCC 55326 | $10^2$ | $10^2$ | $10^2$ |
| Level (4) alone | >$10^4$ | >$10^6$ | >$10^7$ |
| Level (4) + ATCC 55326 | $\leq 10^2$ | $\leq 10^2$ | $\leq 10^2$ |

As can be seen from Table 2, Lactobacillus sp. is very effective in inhibiting *P. putida*, *P. aeruginosa* and other spoilage bacteria in raw milk. It was found that the raw milk was not acidified by lactic acid production at low temperatures.

Example 4

Table 3 shows the results of screening Lactobacillus sp. ATCC 55326 against various food-borne pathogens.

TABLE 3

| Pathogen | Inhibition (+) or No Inhibition (−) |
|---|---|
| 1. *Pseudomonas aeruginosa* | + |
| 2. *Escherichia coli* | + |
| 3. *Salmonella typhimurium* | + |
| 4. *Salmonella enteritidis* | + |
| 5. *Listeria monocytogenes* | − |
| 6. *Pseudomonas putida* ATCC 12633 | + |
| 7. *Pseudomonas nigrificance* | + |
| 8. *Escherichia coli* | + |

The method used was incubation of the milk containing the pathogens ($10^2$/ml) and also containing Lactobacillus sp. AS-1 (ATCC No. 55326) ($10^7$ CFU/ml) anion incubation at 4° C. for 7 days. Pathogens were enumerated by plating on appropriate selective medium.

The advantages of adding Lactobacillus sp. ATCC No. 55326 to raw milk during cold storage are as follows:

(1) Inhibition of Gram negative psychrotrophs, especially Pseudomonas spp. which grow at low temperature and decompose milk fat and proteins and thus affect milk quality. Decomposition of milk components by Pseudomonas spp. during cold storage stimulates the growth of health hazard pathogens such as *Listeria monocytogenes* as discussed by Marshall et al, Can. J. Microbiol. 37, 594–599 (1991).

(2) There is an antagonistic effect on food pathogens, especially Gram-negative bacteria present in low numbers such as Salmonella spp.

(3) There is an energy savings by using holding temperature of 40° F. rather than deep-cooling (36° F.) or thermization as is presently used in the art.

(4) Lactobacillus sp. ATCC No. 55326 added to raw milk at the specified level does not coagulate or significantly acidify raw milk stored at 40° F. for a week.

(5) Raw milk held for a week at 40° F. and containing $10^7$/ml Lactobacillus ATCC No. 55326 does not coagulate nor possess off-flavors when pasteurized. The same advantages are achieved in other foods, particularly dairy products.

The mechanism of inhibition by Lactobacillus sp. ATCC No. 55326 is believed to be by carbon dioxide production. In this regard, Roberts and Torrey (J. Dairy Sci. 71: 52–60 (1988)) reported that refrigerated raw milk containing 20 to 30 millimolar $CO_2$ had significantly lower numbers of Pseudomonas and coliform bacteria than raw milk not treated to contain the $CO_2$. Also, filter sterilized culture supernatants of Lactobacillus species AS-1 (ATCC No. 55326) added to refrigerated (4° C.) raw milk and held for seven (7) days had no inhibitory effect on pathogenic or psychrotrophic bacteria which are inhibited by the viable Lactobacillus AS-1 cells. Such filter-sterilized supernatants also are not inhibitory for these bacteria when tested by the well or disk assay methods. It further was determined that the microorganism does not produce hydrogen peroxide; furthermore, inhibition of psychrotrophs and pathogens occur in the presence of catalase which degrades hydrogen peroxide and that it was not lactic acid production. It appeared that this strain produced an inhibitory effect, possibly by producing copious quantities of $CO_2$ more effectively competing for nutrients than the spoilage bacteria.

It is intended that the foregoing specification be only illustrative of the present invention and that the present invention be limited to the hereinafter appended claims.

We claim:

1. In a method for inhibiting Pseudomonas in a refrigerated food by introducing a bacterium into the food, the improvement which comprises:

providing an effective amount of cells of Lactobacillus sp. ATCC No. 55326 in the refrigerated food to thereby inhibit the Pseudomonas.

2. The method of claim 1 wherein between about $10^6$ and $10^8$ cells per gram are provided in the food.

3. The method of claim 1 wherein the food is refrigerated at between about 4° and 10° C.

4. The method of claim 1 wherein between about $10^6$ and $10^8$ cells per gram are provided in the food which is refrigerated at between about 4° and 10° C.

5. In a method of inhibiting Pseudomonas in refrigerated raw milk by introducing a Lactobacillus into the raw or pasteurized milk the improvement which comprises providing cells of Lactobacillus sp. ATCC No. 55326 in the raw milk, wherein the Lactobacillus sp. inhibit the Pseudomonas in the raw or pasteurized milk.

6. The method of claim 5 wherein between about $10^6$ and $10^8$ cells per ml are provided in the milk.

7. The method of claim 5 wherein the raw milk is refrigerated at the temperature between about 4° and 10° C.

* * * * *